United States Patent
Cincotta

(10) Patent No.: US 9,364,515 B2
(45) Date of Patent: Jun. 14, 2016

(54) THERAPEUTIC PROCESS FOR THE TREATMENT OF THE METABOLIC SYNDROME AND ASSOCIATED METABOLIC DISORDERS

(71) Applicant: VeroScience LLC, Tiverton, RI (US)

(72) Inventor: Anthony H. Cincotta, Tiverton, RI (US)

(73) Assignee: VeroScience LLC, Tiverton, RI (US)

( * ) Notice: Subject to any disclaimer, the term of this patent is extended or adjusted under 35 U.S.C. 154(b) by 0 days.

(21) Appl. No.: 14/447,247

(22) Filed: Jul. 30, 2014

(65) Prior Publication Data

US 2014/0342975 A1    Nov. 20, 2014

Related U.S. Application Data

(60) Division of application No. 13/200,127, filed on Sep. 19, 2011, now Pat. No. 8,821,915, which is a continuation-in-part of application No. 10/944,617, filed on Sep. 17, 2004, now Pat. No. 8,021,681, which is a continuation-in-part of application No. 10/635,841, filed on Aug. 6, 2003, now abandoned.

(60) Provisional application No. 60/402,231, filed on Aug. 9, 2002.

(51) Int. Cl.

| A23L 1/30 | (2006.01) |
|---|---|
| A61K 38/16 | (2006.01) |
| A23L 1/29 | (2006.01) |
| A61K 31/198 | (2006.01) |
| A61K 31/20 | (2006.01) |
| A61K 31/201 | (2006.01) |
| A61K 31/202 | (2006.01) |
| A61K 31/405 | (2006.01) |
| A61K 31/70 | (2006.01) |
| A23L 1/304 | (2006.01) |
| A23L 1/0522 | (2006.01) |
| A23L 1/09 | (2006.01) |

(52) U.S. Cl.
CPC ............ *A61K 38/16* (2013.01); *A23L 1/293* (2013.01); *A23L 1/296* (2013.01); *A61K 31/198* (2013.01); *A61K 31/20* (2013.01); *A61K 31/201* (2013.01); *A61K 31/202* (2013.01); *A61K 31/405* (2013.01); *A61K 31/70* (2013.01); *A23L 1/0522* (2013.01); *A23L 1/09* (2013.01); *A23L 1/304* (2013.01); *A23V 2002/00* (2013.01)

(58) Field of Classification Search
CPC .......... A23L 1/304; A23L 1/0522; A23L 1/09
USPC ................................. 426/72, 2, 74
See application file for complete search history.

(56) References Cited

U.S. PATENT DOCUMENTS

| 4,009,265 A | 2/1977 | Howard |
|---|---|---|
| 4,338,304 A | 7/1982 | Kimimae et al. |
| 4,446,138 A | 5/1984 | Pack |
| 4,659,715 A | 4/1987 | Meier et al. |
| 4,749,709 A | 6/1988 | MeJer et al. |
| 4,783,369 A | 11/1988 | Sugata et al. |
| 4,783,469 A | 11/1988 | Meier et al. |
| 4,791,125 A | 12/1988 | Clark |
| 4,971,969 A | 11/1990 | Carlier et al. |
| 5,006,526 A | 4/1991 | Meier et al. |
| 5,066,495 A | 11/1991 | Moro et al. |
| 5,344,832 A | 9/1994 | Cincotta et al. |
| 5,468,755 A | 11/1995 | Cincotta et al. |
| 5,496,803 A | 3/1996 | Meier et al. |
| 5,554,623 A | 9/1996 | Cincotta et al. |
| 5,565,454 A | 10/1996 | Cincotta |
| 5,585,347 A | 12/1996 | Meier et al. |
| 5,614,492 A | 3/1997 | Habener |
| 5,626,860 A | 5/1997 | Cincotta et al. |
| 5,635,512 A | 6/1997 | Cincotta et al. |
| 5,654,313 A | 8/1997 | Cincotta et al. |
| 5,668,155 A | 9/1997 | Cincotta et al. |
| 5,679,685 A | 10/1997 | Cincotta et al. |
| 5,688,794 A | 11/1997 | Meier et al. |
| 5,696,128 A | 12/1997 | Cincotta et al. |

(Continued)

FOREIGN PATENT DOCUMENTS

| CN | 1678313 | 10/2005 |
|---|---|---|
| CN | 1950078 | 4/2007 |

(Continued)

OTHER PUBLICATIONS

Aellig et al., "Comparative pharmacokinetic investigations with tritium-labeled ergot alkaloids after oral and intravenous administration in man," Int J Clin Pharmacol, 1997, vol. 15, pp. 106-112.

Alford et al., "The effects of variations in carbohydrate, protein, and fat content of the diet upon weight loss, blood values, and nutrient intake of adult obese women," Journal of the American Dietetic Association, Apr. 1990, 90(4):435•540.

Ansel et al., Pharmaceutical Dosage Forms and Drug Delivery Systems, 1995, pp. 78-81.

Armentero et al., "Dopamine Receptor Agonists Media neuroprotection in malonate-Induced striatal lesion in the Rat," Experimental Neurology, Dec. 2002, 178(2):301-305.

(Continued)

*Primary Examiner* — Kevin E Weddington
(74) *Attorney, Agent, or Firm* — Fish & Richardson P.C.

(57) ABSTRACT

The present invention is directed to a method of treating a patient suffering from the metabolic syndrome and/or related disorders including obesity, Type 2 diabetes, pre-diabetes, hypertension, dyslipidemia, insulin resistance, endothelial dysfunction, pro-inflammatory state, and pro-coagulative state, and comprising the steps of (a) providing to the patient a dietary regimen that decreases overactive CNS noradrenergic tone; followed by (b) providing to the patient a dietary regimen that increases dopaminergic tone while maintaining the above decreased overactive CNS noradrenergic tone. The present invention is also directed to food products useful in implementing the dietary regimens.

12 Claims, No Drawings

(56) References Cited

U.S. PATENT DOCUMENTS

| | | |
|---|---|---|
| 5,700,795 A | 12/1997 | Cincotta et al. |
| 5,700,800 A | 12/1997 | Cincotta et al. |
| 5,712,265 A | 1/1998 | Cincotta et al. |
| 5,714,519 A | 2/1998 | Cincotta et al. |
| 5,716,957 A | 2/1998 | Cincotta et al. |
| 5,716,962 A | 2/1998 | Cincotta et al. |
| 5,719,160 A | 2/1998 | Cincotta et al. |
| 5,731,312 A | 3/1998 | Cincotta et al. |
| 5,741,503 A | 4/1998 | Cincotta et al. |
| 5,744,477 A | 4/1998 | Cincotta et al. |
| 5,750,519 A | 5/1998 | Cincotta et al. |
| 5,756,513 A | 5/1998 | Cincotta et al. |
| 5,760,047 A | 6/1998 | Cincotta et al. |
| 5,792,748 A | 8/1998 | Cincotta et al. |
| 5,830,895 A | 11/1998 | Cincotta et al. |
| 5,854,255 A | 12/1998 | Cincotta et al. |
| 5,866,584 A | 2/1999 | Cincotta et al. |
| 5,872,127 A | 2/1999 | Cincotta et al. |
| 5,872,133 A | 2/1999 | Cincotta et al. |
| 5,877,183 A | 3/1999 | Cincotta |
| 5,902,811 A | 5/1999 | Cincotta |
| 5,905,083 A | 5/1999 | Cincotta et al. |
| 6,004,972 A | 12/1999 | Cincotta et al. |
| 6,011,049 A | 1/2000 | Whitcomb |
| 6,040,292 A | 3/2000 | Sommer |
| 6,071,914 A | 6/2000 | Cincotta et al. |
| 6,075,020 A | 6/2000 | Cincotta et al. |
| 6,166,017 A | 12/2000 | Marin |
| 6,197,765 B1 | 3/2001 | Vardi et al. |
| 6,248,375 B1 | 6/2001 | Gilles et al. |
| 6,277,887 B1 | 8/2001 | Yong |
| 6,322,976 B1 | 11/2001 | Altman et al. |
| 6,365,176 B1 | 4/2002 | Bell et al. |
| 6,376,464 B1 | 4/2002 | Dasseux et al. |
| 6,410,339 B1 | 6/2002 | Marin |
| 6,441,036 B1 | 8/2002 | Berge |
| 6,506,799 B1 | 1/2003 | Dasseux |
| 6,855,707 B2 | 2/2005 | Cincotta |
| 7,223,728 B2 | 5/2007 | Yakubu-Madus et al. |
| 7,258,871 B2 | 8/2007 | Horowski et al. |
| 7,572,789 B2 | 8/2009 | Cowen et al. |
| 7,888,310 B2 | 2/2011 | Cincotta |
| 8,021,681 B2 | 9/2011 | Cincotta |
| 8,137,992 B2 | 3/2012 | Cincotta |
| 8,137,993 B2 | 3/2012 | Cincotta |
| 8,137,994 B2 | 3/2012 | Cincotta |
| 8,431,155 B1 | 4/2013 | Cincotta et al. |
| 8,613,947 B2 | 12/2013 | Cincotta et al. |
| 8,741,918 B2 | 6/2014 | Cincotta |
| 8,821,915 B2 | 9/2014 | Cincotta |
| 8,877,708 B2 | 11/2014 | Cincotta |
| 2001/0002269 A1 | 5/2001 | Zhao |
| 2002/0187985 A1 | 12/2002 | Cincotta |
| 2003/0087963 A1 | 5/2003 | Senanayake et al. |
| 2003/0212085 A1 | 11/2003 | McCall et al. |
| 2004/0180088 A1 | 9/2004 | Dudhara et al. |
| 2004/0214887 A1 | 10/2004 | Dasseux et al. |
| 2004/0220190 A1 | 11/2004 | Cincotta |
| 2005/0054652 A1 | 3/2005 | Cincotta |
| 2005/0220855 A1 | 10/2005 | Horowski et al. |
| 2005/0232989 A1 | 10/2005 | Piene et al. |
| 2005/0245612 A1 | 11/2005 | Blass |
| 2006/0057207 A1 | 3/2006 | Ziegler et al. |
| 2006/0111348 A1 | 5/2006 | Kampen et al. |
| 2006/0239928 A1 | 10/2006 | Heit et al. |
| 2007/0129312 A1 | 6/2007 | Yatvin et al. |
| 2007/0191371 A1 | 8/2007 | Bennet et al. |
| 2007/0225379 A1 | 9/2007 | Carrara et al. |
| 2007/0292479 A1 | 12/2007 | Podhaisky et al. |
| 2008/0200453 A1 | 8/2008 | Cincotta |
| 2008/0293735 A1 | 11/2008 | Cincotta |
| 2009/0143390 A1 | 6/2009 | Cincotta |
| 2009/0305225 A1 | 12/2009 | Galbraith |
| 2010/0035886 A1 | 2/2010 | Cincotta et al. |
| 2012/0148499 A1 | 6/2012 | Tsien et al. |
| 2012/0283193 A1 | 11/2012 | Spitzer et al. |
| 2013/0197005 A1 | 8/2013 | Cincotta |
| 2014/0249136 A1 | 9/2014 | Cincotta |

FOREIGN PATENT DOCUMENTS

| | | |
|---|---|---|
| EP | 1004594 | 5/2000 |
| JP | 9301892 | 11/1997 |
| JP | 2002539163 | 11/2002 |
| JP | 2005-533768 | 11/2005 |
| JP | 2007502823 | 2/2007 |
| JP | 2010-157037 | 2/2010 |
| KR | 20100091944 | 8/2010 |
| RU | 2467743 | 11/2012 |
| WO | 9312701 | 7/1993 |
| WO | 9312793 | 7/1993 |
| WO | 9415211 | 7/1994 |
| WO | 9517170 | 6/1995 |
| WO | 9518614 | 7/1995 |
| WO | 9600396 | 1/1996 |
| WO | 9613251 | 5/1996 |
| WO | 9639050 | 12/1996 |
| WO | 9639052 | 12/1996 |
| WO | 9639868 | 12/1996 |
| WO | 9706786 | 2/1997 |
| WO | 9741873 | 11/1997 |
| WO | 9808871 | 3/1998 |
| WO | 9831368 | 7/1998 |
| WO | 0032171 | 6/2000 |
| WO | 0054774 | 9/2000 |
| WO | 2004010946 | 2/2004 |
| WO | 2005016321 | 2/2005 |
| WO | 2005049088 | 6/2005 |
| WO | 2005120492 | 12/2005 |
| WO | 2006103417 | 10/2006 |
| WO | 2006128022 | 11/2006 |
| WO | 2007085498 | 8/2007 |
| WO | 2007140191 | 12/2007 |
| WO | 2009091576 | 7/2009 |

OTHER PUBLICATIONS

Arteriosclerosis/atherosclerosis Definition-Diseases and Condition, by Mayo Clinic staff, May 2014, accessed on Oct. 8, 2014, available at http://www.mayoclinic.org/diseases-conditions/arteriosclerosis-atherosclerosis/basics/definition/con-20026972, 9 pages.

Australian Office Action in AU Application No. 2009205641, dated Sep. 25, 2014, 4 pages.

Australian Office Action in AU Application No. 2009205641, dated Jul. 3, 2014, 4 pages.

Australian Office Action in AU Application No. 2013256558, dated Jan. 30, 2015, 2 pages.

"Alternative Routes of Drug Administration—Advantages and Disadvantages (Subject Review)," Pediatrics, 1997, 100(1):10 pages.

Baba et al., "High protein vs high carbohydrate hypoenergetic diet for the treatment of obese hyperinsulinemic subjects", International Journal of Obesity, Nov. 199, vol. 23, pp. 1202•1206.

Benes et al., "Transmucosal, oral controlled-release, and transdermal drug administration in subjects: a crossover study with melatonin," Journal of Pharmaceutical Sciences, Oct. 1997,86(10):1115-1119.

Breen et al., "Insulin increases reendothelialization and inhibits cell migration and neointimal growth after arterial injury," Arterioscler Thromb Vasc Biol. 2009, 29:1060-1066.

Bruemmer et al., "Thiazolidinedione regulation of smooth muscle cell proliferation," The American Journal of Medicine, Dec. 8, 2003, 115(BA):87S-92S.

Canadian Office Action in CA Application No. 2,749,611, dated Mar. 17, 2015, 3 pages.

Canadian Office Action in CA Application No. 2,872,300, dated May 27, 2015, 2 pages.

Carranza et al., "L-Dopa uptake and dopamine production in proximal tubular cells are regulated by ~2-adrenergic receptors," Am J Physiol Renal Physiol, 279: F77-F83, 2000.

Cavero et al., "Heart rate lowering effects of N, N-di-n-Propyl-dopamine in rats: evidence for stimulation of central dopamine receptors leading to inhibition of sympathetic tone and enhancement of

(56) References Cited

OTHER PUBLICATIONS parasympathetic outflow," Journal of Pharmacology and Experimental Therapeutics, 1981, 219(2):510-519.
Chinese Office Action in CN Application No. 200980108993.1, dated Aug. 23, 2012, 6 pages (with English translation).
Chinese Office Action in CN Application No. 200980108993.1, dated Apr. 24, 2013, 8 pages (with English translation).
Chinese Office Action in CN Application No. 200980108993.1, dated Nov. 26, 2013, 5 pages (with English translation).
Chinese Office Action in CN Application No. 200980108993.1, dated Sep. 2, 2014, 6 pages (with English translation).
Chinese Office Action in CN Application No. 200980108993.1, dated Aug. 18, 2011, 7 pages (with English translation).
Ciccarelli et al., "Double blind randomized study using oral or injectable bromocriptine in patients with hyperprolactinaemia," Clinical Endocrinol, 1994, vol. 40, pp. 193-198.
Cicinelli et al., "Nasal spray administration of bromocriptine: pharmacology and effect on serum prolactin level in puerperal women," Gynecol Endocrinol, 1996, vol. 10, pp. 391-396.
Cicinelli et al., "Nasal spray bromocriptine: Effects on serum prolactin in puerperal women," Acta Obstet Gynecol Scand, 1996, 75:730-733.
Cicinelli et al., "Nasal spray vs oral administration of bromocriptine: Pharmacology and effect on serum prolactin in puerperal woman," J Endocrinol Invest, 1996, vol. 19, pp. 427-432.
Cincotta et al., "Bromocriptine improves glycaemic control and serum lipid profile in obese Type 2 diabetic subjects: a new approach in the treatment of diabetes," Expert Opinion on Investigational Drugs, Ashley Publications Ltd., United Kingdom, 1999, 8(10):1683-1707.
Communication Pursuant to Article 94(3) EPC issued in EP Application No. 08768002.1, dated Jan. 15, 2014, 7 pages.
Communication Pursuant to Article 94(3) EPC issued in EP Application No. 08768002.1, dated Apr. 20, 2011, 4 pages.
Communication Pursuant to Article 94(3) EPC issued in EP Application No. 08742225.9, dated Dec. 23, 2014, 4 pages.
Dai et al., "LOX-1, a bridge between GLP-1 and mitochondrial ROS generation in human vascular smooth muscle cells," Biochemical and Biophysical Research Communications, 2013, 437:62-66.
Degim et al., "Transdermal administration of bromocriptine," Biol Pharm Bull, 2003, vol. 26, pp. 501-505.
Dios et al., "Troglitazone, but not rosiglitazone, inhibits na/h exchange activity and proliferation of macrovascular endothelial cells," Journal of Diabetes and its Complications, 2001, 15:120-127.
Dormandy et al., "Secondary prevention of macrovascular events in patients with type 2 diabetes in the PROactive Study (PROspective pioglitazone Clinical Trial in macrovascular events): a randomised controlled trial," Lancet, Oct. 8, 2005, 366:1279-89.
Dubey et al., "Pioglitazone attenuates hypertension and inhibits growth of renal arteriolar smooth muscle in rats," American Physiological Society, 1993, R726-R732.
Duckworth et al., "Glucose control and vascular complications in veterans with type 2 diabetes," The New England Journal of Medicine, Jan. 8, 2009, 360:129-139.
Durant et al., "Bromocriptine-Induced Hyperglycemia in Nonobese Diabetic Mice: Kinetics and Mechanisms of Action," The Review of Diabetic Studies, 2007, vol. 4, pp. 185-194.
Durif et al., "Efficacy of sublingual apomorphine in Parkinson's disease," J Neurol Neurosurg Psych, 1990, vol. 53, p. 1105.
English translation of Chinese article entitled: Compatibility of dopamine hydrochloride and inosine in transfusion: Journal of Medical Science Yanbian University, Feb. 1998, vol. 21, No. 2, p. 102.
Ervinna et al., "Anagliptin, a dpp-4 inhibitor, suppresses proliferation of vascular smooth muscles and monocyte inflammatory reaction and attenuates atherosclerosis in male apo e-deficient mice," Endocrinology, Mar. 2013, 145(3):1260-1270.
European Office Action in EP Application No. 02018888.4, dated Aug. 4, 2011, 5 pages.
European Office Action in EP Application No. 10190054.6, dated Sep. 25, 2015, 9 pages.
European Office Action in EP Application No. 13721874.9, dated Dec. 9, 2014, 2 pages.
Ex Parte Quayle Office Action in U.S. Appl. No. 13/774,739, dated May 6, 2015, 5 pages.
Examination Report issued in AU Application No. 2013263800, dated Sep. 2, 2015, 3 pages.
Extended European Search Report in EP Application No. 11792943.0, dated Oct. 30, 2013, 5 pages.
Extended European Search Report in EP Application No. 08780943.0, dated Dec. 20, 2013, 7 pages.
Extended European Search Report in EP Application No. 10190054.6, dated Mar. 22, 2011, 10 pages.
Extended European Search Report in EP Application No. 08742225.9, dated Oct. 15, 2010, 12 pages.
Extended European Search Report in EP Application No. 08768002.1, dated Jul. 8, 2010, 7 pages.
Final Office Action in U.S. Appl. No. 10/944,617, dated Aug. 18, 2009, 15 pages.
Final Office Action in U.S. Appl. No. 12/144,617, dated Dec. 6, 2011, 8 pages.
Final Office Action in U.S. Appl. No. 12/144,620, dated Jan. 27, 2012, 22 pages.
Final Office Action in U.S. Appl. No. 12/154,907, dated Jun. 12, 2012, 11 pages.
Final Office Action in U.S. Appl. No. 12/154,907, dated Jun. 19, 2014, 23 pages.
Final Office Action in U.S. Appl. No. 12/402,694, dated May 17, 2012, 41 pages.
Final Office Action in U.S. Appl. No. 13/774,739, dated Oct. 21, 2014, 6 pages.
Final Office Action in U.S. Appl. No. 13/799,138, dated Apr. 7, 2014, 42 pages.
Final Office Action in U.S. Appl. No. 13/799,138, dated Sep. 29, 2015, 52 pages.
Final Office Action in U.S. Appl. No. 12/077,552, dated Oct. 22, 2014, 22 pages.
Final Office Action in U.S. Appl. No. 12/077,552, dated Jul. 16, 2013, 13 pages.
Final Office Action in U.S. Appl. No. 12/077,552, dated Apr. 10, 2012, 12 pages.
Final Office Action in U.S. Appl. No. 12/322,319, dated Mar. 24, 2010, 4 pages.
Final Office Action in U.S. Appl. No. 13/375,810, dated Jan. 3, 2014, 9 pages.
Final Office Action in U.S. Appl. No. 13/885,006, dated Jun. 16, 2015, 17 pages.
Final Office Action in U.S. Appl. No. 11/086,937, dated Jan. 18, 2008, 5 pages.
Final Office Action in U.S. Appl. No. 10/627,014, dated Mar. 11, 2008, 9 pages.
Final Office Action in U.S. Appl. No. 10/635,841, dated Jun. 27, 2007, 9 pages.
First Examination Report in IN Application No. 7696/DELNP/2009, dated Jan. 7, 2015, 2 pages.
First Office Action in CN Application No. 200880025452.8, dated Apr. 19, 2012, 11 pages (with English translation).
Fluckiger, E., Editorial Note, 1992, Experiential, 48:248.
Fourth Office Action in CN Application No. 200880025452.8, dated Jan. 22, 2015, 14 pages (with English translation).
Freedman et al., "Popular Diets: A Scientific view", Obesity Research, Mar. 2001, vol. 9, Supp. 1, pp. IS•40S.
Fukuda et al., "Troglitazone inhibits growth and improves insulin signaling by suppression of angiotensin ii action in vascular smooth muscle cells from spontaneously hypertensive rats," Atherosclerosis, 2002, 11 pages.
Gadde et al., "Bupropion for weight loss: an investigation of efficacy and tolerability in overweight and obese women," Obesity Research, Sep. 2001, 9(9):544-551.
Garcia-Robles et al., "Dopamine control of aldosterone secretion in end-stage renal failure," Rev Esp Fisiol, 1986, 42(2):257-63.
Gaziano et al., "Effect of bromocriptine-qr (a quick-release formulation of bromocriptine mesylate) on major adverse cardiovascular events in type 2 diabetes subjects," J Am Heart Assoc, 2012, 11 pages.

(56) References Cited

OTHER PUBLICATIONS

Gaziano et al., "Randomized clinical trial of quick-release bromocriptine among patients with type 2 diabetes on overall safety and cardiovascular outcomes," Diabetes Care, Jul. 2010, 33:1503-1508 (12 total pages).
Gerstein et al., "Effects of intensive glucose lowering in type 2 diabetes," The New England Journal of Medicine, Jun. 12, 2008, 358:2545-59.
Gerstein, "Basal insulin and cardiovascular and other outcomes in dysglycemia," The New England Journal of Medicine, Jul. 26, 2012, 367:319-328.
Goto et al., "Exendin-4, a glucagon-like peptide-1 receptor agonist, reduces intimal thickening after vascular injury," Biochemical and Biophysical Research Communications, 2011, 405:79-84.
Gouni-Berthold et al., "Troglitazone and rosiglitazone inhibit the low density lipoprotein-induced vascular smooth muscle cell growth," Exp Clin Endocrinol Diabetes, 2001, 109:203-209.
Grundy, "Drug therapy of the metabolic syndrome: minimizing the emerging crisis in polypharmacy," Nature Reviews/Drug Discovery, vol. 5, Apr. 2006, pp. 295-309.
Ha et al., "High glucose induces connective tissue growth factor expression and extracellular matrix accumulation in rat aorta vascular smooth muscle cells via extracellular signal-regulated kinase 1 / 2," Korean J Physiol Pharmacol, Aug. 2013, 17:307-314.
Haase et al., "Control of prolactin-secreting macroadenomas with parenteral long-acting bromocriptine in 30 patients treated for up to 3 years," Clinical Endocrinology, 1993, 38(2):165-176.
Hara et al., "Central dopam\inergic function in stroke prone spontaneously hypertensive rats effects of chronic treatment with lisuride on the impaired swimming ability," Database Accession No. PREV198376013141 and Folia Pharmacologica Japonica, 1982, 80(5):395-394 (Abstract only—2 pages).
Hasko et al., "Modulation of lipopolysaccharide-induced tumor necrosis factor-α and nitric oxide production by dopamine receptor agonists and antagonists in mice," Immunology Letters, 1996, 49(3):143-147.
Hisahara et al., "Review Article Dopamine Receptors and Parkinson's Disease," International Journal of Medicinal Chemistry, 2011, 16 pages.
Home et al., "Rosiglitazone evaluated for cardiovascular outcomes in oral agent combination therapy for type 2 diabetes (record): a multicentre, randomised, open-label trial," Lancet, Jun. 20, 2009, 373:2125-35.
Hsueh et al., "Insulin signaling in the arterial wall," Am J Cardiol, 1999, 84:21J-24J.
Humbert et al., "Human pharmacokinetics of dihydroergotamine administered by nasal spray," Clin Pharmacol Ther, 1996, vol. 60, pp. 265-275.
Indian Office Action in IN Application No. 2989/KOLNP/2010, dated Oct. 9, 2015, 11 pages (with English translation).
International Preliminary Examination Report in PCT Application No. PCTUS2003024933, dated Apr. 6, 2004, 3 pages.
International Preliminary Examination Report in PCT Application No. PCTUS0323662, dated Oct. 21, 2004, 3 pages.
International Preliminary Report on Patentability in International Application No. PCT/US2008/067953, dated Dec. 22, 2009, 5 pages.
International Preliminary Report on Patentability in International Application No. PCT/US2009/000268, dated Jul. 20, 2010, 11 pages.
International Preliminary Report on Patentability in International Application No. PCT/US2013/038655, dated Nov. 4, 2014, 9 pages.
International Preliminary Report on Patentability in PCT Application No. PCTUS201139215, dated Dec. 10, 2012, 7 pages.
International Preliminary Report on Patentability issued in International Application No. PCT/US2008/006899, issued Dec. 1, 2009, 7 pages.
International Preliminary Report on Patentability issued in International Application No. PCT/US2008/003849, issued Oct. 6, 2009, 7 pages.
International Preliminary Report on Patentability in PCT Application No. PCT/US2011/61586, dated May 28, 2013, 5 pages.
International Search Report and Written Opinion in International Application No. PCT/US2009/000268, dated Apr. 7, 2010, 16 pages.
International Search Report and Written Opinion in International Application No. PCT/US2008/067953, dated Nov. 3, 2008, 5 pages.
International Search Report and Written Opinion in International Application No. PCT/US2013/038655, dated Jul. 2, 2013, 12 pages.
International Search Report and Written Opinion issued in International Application No. PCT/US2008/006899, dated Aug. 29, 2008, 7 pages.
International Search Report and Written Opinion issued in International Application No. PCT/US2008/003849, dated Jun. 20, 2008, 7 pages.
International Search Report in PCT Application No. PCTUS0323662, dated Apr. 21, 2004, 1 page.
International Search Report in PCT Application No. PCTUS2003024933, dated Dec. 10, 2003, 1 page.
International Search Report in PCT Application No. PCTUS201139215, dated Dec. 1, 2011, 10 pages.
International Search Report which issued Oct. 10, 2014 in corresponding WO application No. PCT US2014/042397, 12 pages.
International Preliminary Report on Patentability in PCT US2014/042397, dated Dec. 15, 2015.
International Search Report and Written Opinion in PCT Application No. PCT/US2011/61586, dated Mar. 22, 2012, 8 pages.
Israeli Office Action in IL Application No. 207001, dated Jan. 28, 2014, 7 pages (with English translation).
Israeli Office Action in IL Application No. 207001, dated Jan. 21, 2013, 2 pages (with English translation).
Japanese Office Action in JP Application No. 2010-543138, dated Jul. 30, 2013, 7 pages (with English translation).
Japanese Office Action in JP Application No. 2010-543138, dated Aug. 15, 2014, 2 pages (with English translation).
Japanese Office Action in JP Application No. 2014-13265, dated Feb. 3, 2015, 5 pages (with English translation).
Japanese Office Action in JP Application No. 2014-13266, dated Feb. 3, 2015, 4 pages (with English translation).
Jaspers et al., "Long term treatment of acromegalic patients with repeatable parenteral depot-bromocriptine," Clin Investig, 1993, vol. 71, pp. 547-551.
Katz et al., "Successful treatment of a prolactin-producing pituitary macroadenoma with intravaginal bromocriptine mesylate: A novel approach to intolerance of oral therapy," Obstet Gynecol, 1989, vol. 73, pp. 517-520.
Kharkevich, DA, Pharmacology (textbook), Moscow, GAOTAR-Media (2006), pp. 39 and 44.
Kihara et al., "ProtectiveEffectofDopamineD2Agonists in Cortica Neurons Via the Phosphatidylinositol 3 Kinase Cascade," J. Neurosci Res, 2002, 70:274-282.
Kok et al., "Activation of dopamine D2 receptors simultaneously ameliorates various metabolic features of obese women," American Journal of Physiology—Endocrinology and Metabolism, vol. 291, Jun. 27, 2006, pp. E1038-E1043.
Korean Office Action in KR Application No. 10-2014-7033501, dated Mar. 11, 2015, 22 pages (with English translation).
Kuo et al., "Hypothalamic neuropeptide Y (NPY) and the attenuation of hyperphagia in streptozotocin diabetic rats treated with dopamine D1/D2 agonists," British Journal of Pharmacology, 2006, 148:640-647.
Lam et al., "Activation of N-Methyl-D-aspartate (NMDA) Receptors in the Dorsal Vagal Complex Lowers Glucose Production," J Biol Chem, Jul. 16, 2010, 285(29): 21913-21921.
Lan et al., "Vascular fibrosis in atherosclerosis," Cardiovascular Pathology, 2013, 22:4101-407.
Li et al., "GLP-1 receptor stimulation preserves primary cortical and dopaminergic neurons in cellular and and rodent models of stroke and parkinsonism," PNAS, Jan. 2009, vol. 106, 1285-1290.
Lightell et al., "Loss of canonical insulin signaling accelerates vascular smooth muscle cell proliferation and migration through changes in p27kip1 regulation," Endocrinology, Feb. 2011, 152(2):651-658.
Kalra et al., "Dopamine: The Forgotten Felon in Type 2 Diabetes," Recent Patents on Endocrine, Metabolic & Immune Drug Discovery, 2011, 5(1):61-65.

(56) References Cited

OTHER PUBLICATIONS

Lusis, "Atherosclerosis," Nature, Sep. 2000, 407(6801): 233-241.
Mannelli et al., "Effects of different dopaminergic antagonists on bromocriptine-induced inhibition of norepinephrine release," Journal of Clinical Endocrinology and Metabolism, 1984, 59(1):74-78.
Mattox et al., "Dopamine Agonists for Reducing Depression Associated with Hyperprolactinemia," The Journal of Medicine, Aug. 1988, 31(8):694-698.
Meier et al., "Timed bromocriptine administration reduces body fat stores in obese subjects and hyperglycemia in type II diabetes," Experientia, 1992, 48(3):248-253.
Mexican Office Action in MX Application No. MX/A/2010/007741, dated Mar. 8, 2012, 5 pages (English translation only).
Mexican Office Action in MX Application No. MX/A/2010/007741, dated Jul. 19, 2013, 8 pages (English translation only).
Mexican Office Action in MX Application No. MX/A/2010/007741, dated Mar. 4, 2014, 8 pages (with English translation).
Mexican Office Action in MX Application No. MX/A/2010/007741, dated Dec. 1, 2014, 6 pages (with English translation).
Narkar et al., "Dopamine D2-like receptor against bromocriptine protects against ischemia/reperfusion injury in rat kidney," Kidney International, 2004, vol. 66, pp. 633-640.
NCBI Reference Sequence XP-002587257, Hypothetical Protein BRAFLDRAFT-61678 (Branchiostoma floridae), Accession No. XP_002587257, GI No. 260784404, dated Oct. 8, 2009, (retrieved from the Internet: Feb. 23, 2015), 2 pages.
Nielsen et al., "Desipramine and Some Other Antidepressant Drugs Decrease the Major Norepinephrine Metabolite 3,4-Dihydroxyphenylglycol-Sulphate in the Rat Brain," Naunyn-Schmiedeberg's Archives of Pharmacology, 1977, vol. 300, pp. 93-99.
NIH Publication No. 05-4642 [online], www.diabetes.niddk.nih.gov, Jan. 2005 [retrieved on Nov. 6, 2011]. Retrieved from the Internet: <URL: http://diabetes.niddk.nih gov/d m/pubs/d iag nosis/., 7 pages.
Non-final Office Action in U.S. Appl. No. 10/944,617, dated Nov. 25, 2008, 17 pages.
Non-final Office Action in U.S. Appl. No. 10/944,617, dated Sep. 7, 2010, 5 pages.
Non-final Office Action in U.S. Appl. No. 12/144,617, dated May 4, 2011, 12 pages.
Non-final Office Action in U.S. Appl. No. 12/144,620, dated Jun. 9, 2011, 14 pages.
Non-final Office Action in U.S. Appl. No. 12/154,907, dated Mar. 23, 2015, 16 pages.
Non-final Office Action in U.S. Appl. No. 12/154,907, dated Sep. 15, 2011, 14 pages.
Non-final Office Action in U.S. Appl. No. 12/154,907, dated Sep. 12, 2013, 19 pages.
Non-final Office Action in U.S. Appl. No. 12/402,694, dated Dec. 5, 2014, 46 pages.
Non-final Office Action in U.S. Appl. No. 12/402,694, dated Sep. 1, 2011, 37 pages.
Non-final Office Action in U.S. Appl. No. 13/460,452, dated Sep. 17, 2012, 11 pages.
Non-final Office Action in U.S. Appl. No. 13/773,500, dated May 2, 2013, 12 pages.
Non-final Office Action in U.S. Appl. No. 13/774,739, dated Mar. 20, 2014, 14 pages.
Non-final Office Action in U.S. Appl. No. 13/799,138, dated May 13, 2015, 53 pages.
Non-final Office Action in U.S. Appl. No. 13/799,138, dated Oct. 18, 2013, 50 pages.
Non-final Office Action in U.S. Appl. No. 14/088,269, dated Dec. 5, 2014, 10 pages.
Non-final Office Action in U.S. Appl. No. 13/200,127, dated Feb. 22, 2013, 10 pages.
Non-final Office Action in U.S. Appl. No. 13/200,127, dated Jul. 23, 2013, 6 pages.
Non-final Office Action in U.S. Appl. No. 12/077,552, dated Sep. 15, 2015, 39 pages.
Non-final Office Action in U.S. Appl. No. 12/077,552, dated Feb. 10, 2014, 10 pages.
Non-final Office Action in U.S. Appl. No. 12/077,552, dated Jul. 7, 2011, 10 pages.
Non-final Office Action in U.S. Appl. No. 12/322,319, dated Jun. 2, 2009, 7 pages.
Non-final Office Action in U.S. Appl. No. 12/931,859, dated May 19, 2011, 9 pages.
Non-final Office Action in U.S. Appl. No. 13/066,255, dated May 19, 2011, 8 pages.
Non-final Office Action in U.S. Appl. No. 13/066,280, dated Aug. 9, 2011, 7 pages.
Non-final Office Action in U.S. Appl. No. 13/885,006, dated Nov. 5, 2014, 14 pages.
Non-final Office Action in U.S. Appl. No. 13/375,810, dated May 13, 2013, 20 pages.
Non-final Office Action in U.S. Appl. No. 11/086,937, dated Jun. 13, 2007, 5 pages.
Non-final Office Action in U.S. Appl. No. 10/627,014, dated Jun. 11, 2007, 9 pages.
Non-final Office Action in U.S. Appl. No. 10/635,841, Oct. 4, 2006, 10 pages.
Non-final Office Action in U.S. Appl. No. 10/635,841, dated Feb. 26, 2008, 11 pages.
Nordin et al., "Bromocriptine treatment of depressive disorders,",Acta psychiatrica Scandinavica, 1981,64(1):25-33.
Notice of Allowance in U.S. Appl. No. 12/931,859, dated Nov. 17, 2011, 6 pages.
Notice of Allowance in U.S. Appl. No. 13/066,280, dated Nov. 29, 2011, 6 pages.
Notice of Allowance in U.S. Appl. No. 10/944,617, dated May 17, 2011, 5 pages.
Notice of Allowance in U.S. Appl. No. 12/322,319, dated Oct. 12, 2010, 4 pages.
Notice of Allowance in U.S. Appl. No. 13/066,255, dated Dec. 12, 2011, 6 pages.
Notice of Allowance in U.S. Appl. No. 13/200,127, dated Dec. 16, 2013, 7 pages.
Notice of Allowance in U.S. Appl. No. 13/375,810, dated Jul. 2, 2014, 7 pages.
Notice of Allowance in U.S. Appl. No. 13/460,452, dated Mar. 6, 2013, 13 pages.
Notice of Allowance in U.S. Appl. No. 13/744,739, dated Aug. 3, 2015, 5 pages.
Notice of Allowance in U.S. Appl. No. 13/773,500, dated Sep. 16, 2013, 10 pages.
Notice of Allowance in U.S. Appl. No. 14/088,269, dated Jul. 27, 2015, 13 pages.
O'Neill et al., "Dopamine D2 receptor agonists protect against ischaemia induced hippocampal neurodegeneration in global cerebral ischaemia," European Journal of Pharmacology, Jul. 3, 1998, 352(1):37-46.
Office Action in CN Application No. 201180035790.1, dated Nov. 20, 2013, 20 pages (with English translation).
Office Action in EP Application No. 03785088.0, dated Jun. 1, 2010, 8 pages.
Office Action in CA Application No. 2,688,035, dated Aug. 13, 2015, 4 pages.
Office Action in CA Application No. 2,688,035, dated Jan. 7, 2014, 2 pages.
Office Action in CA Application No. 2,693,254, dated Jul. 15, 2015, 3 pages.
Office Action in JP Application No. 2010-510366, dated Jun. 10, 2014, 8 pages (with English translation).
Office Action in JP Application No. 2010-510366, dated Oct. 4, 2013, 5 pages (with English translation).
Office Action in JP Application No. 2014-018636, dated Mar. 10, 2015, 8 pages (with English translation).
Office Action in MX Application No. MX/a/2009/012919, dated Sep. 19, 2011, 3 pages (with English translation).
Office Action in MX Application No. MX/a/2009/012919, dated Jun. 5, 2012, 6 pages (with English translation).

(56) References Cited

OTHER PUBLICATIONS

Office Action in MX Application No. MX/a/2009/012919, dated Feb. 11, 2013, 7 pages (with English translation).
Office Action in MX Application No. MX/a/2009/012919, dated Sep. 3, 2013, 7 pages (with English translation).
Office Action in RU Application No. 2010134158, dated Feb. 8, 2013, 5 pages.
Official Action in IL Application No. 202269, dated Dec. 24, 2014, 4 pages (with English translation).
Official Action in IL Application No. 202269, dated Feb. 19, 2014, 5 pages (with English translation).
Ondo et al., "A novel sublingual apomorphine treatment for treatment for patients with fluctuating Parkinson's disease," Movement Disorders, 1999, vol. 14, pp. 664-668.
Opposition filed by Indian Pharmaceutical Alliance against corresponding Indian Patent Application No. 7696/DELNP/2009 (owned by VeroScience, LLC), Jan. 3, 2011, 38 pages.
Park et al., "The inhibition of insulin-stimulated proliferation of vascular smooth muscle cells by rosiglitazone is mediated by the akt-mtor-p70s6k pathway," Yonsei Med J, 2008, 49(4):592-600.
Patel et al., "Intensive blood glucose control and vascular outcomes in patients with type 2 diabetes," The New England Journal of Medicine, Jun. 6, 2008, 358:2560-72.
Peces et al., "Prolactin in chronic renal failure, haemodialysis, and transplant patients," Pro. EDTA, 1979, 16:700-702.
Piacentini et al., "Effect of bupropion on hippocampal neurotransmitters and on peripheral hormonal concentrations in the rat," Journal of Applied Physiology, vol. 95, 2003, pp. 652-656.
Pietz et al. "Paper Subcutaneous apomorphine in late stage Parkinson's disease: a long term follow up," J Neurol Neurosurg Psychiatry, 1998, 65:709-716.
Pijl and Meinders, "Modulation of monoaminergic neural circuits: potential for the treatment of type 2 diabetes mellitus," Treat Endocrine, 2002, 1(2):71-78.
Pjil et al., "Bromocriptine: a novel approach to the treatment of type 2 diabetes," Erner. Treat., Tech., Aug. 2000, 23(8):1154-1161.
Ratner et al., "Cardiovascular safety of exenatide BID: an integrated analysis from controlled clinical trials in participants with type 2 diabetes," Cardiovascular Diabetology, 2011, 10:22, 10 pages.
Raymond et al., "Pharmacotherapeutic Options for the Treatment of Depression in Patients With Chronic Kidney Disease," Nephrology Nursing Journal, 2008, 35(3):257-264.
Reavill et al., "Metabolite involvement in bromocriptine-induced circling behaviour in rodents," J. Pharm. Pharmacol., 1980, vol. 32, pp. 278-284.
Restriction Requirement in U.S. Appl. No. 10/944,617, dated May 19, 2008, 9 pages.
Restriction Requirement in U.S. Appl. No. 12/144,617, dated Jan. 20, 2011, 7 pages.
Restriction Requirement in U.S. Appl. No. 12/144,620, dated Mar. 1, 2011, 10 pages.
Restriction Requirement in U.S. Appl. No. 12/154,907, dated Apr. 15, 2011, 11 pages.
Restriction Requirement in U.S. Appl. No. 12/402,694, dated Mar. 3, 2011, 11 pages.
Restriction Requirement in U.S. Appl. No. 13/200,127, dated Dec. 7, 2012, 7 pages.
Restriction Requirement in U.S. Appl. No. 13/375,810, dated Feb. 1, 2013, 10 pages.
Restriction Requirement in U.S. Appl. No. 13/701,872, dated Jun. 26, 2015, 12 pages.
Restriction Requirement in U.S. Appl. No. 13/774,739, dated Dec. 10, 2013, 7 pages.
Restriction Requirement in U.S. Appl. No. 13/799,138, dated May 16, 2013, 5 pages.
Restriction Requirement in U.S. Appl. No. 14/272,130, dated Oct. 2, 2015, 6 pages.
Restriction Requirement in U.S. Appl. No. 10/944,631, dated Jun. 20, 2008, 6 pages.
Restriction Requirement in U.S. Appl. No. 10/821,233, dated Apr. 2, 2008, 16 pages.
Restriction Requirement in U.S. Appl. No. 10/944,660, dated May 12, 2008, 10 pages.
Restriction Requirement in U.S. Appl. No. 10/627,014, dated Aug. 25, 2006, 6 pages.
Restriction Requirement in U.S. Appl. No. 10/627,014, dated Jan. 3, 2007, 6 pages.
Restriction Requirements in U.S. Appl. No. 10/635,841, dated Mar. 14, 2006, 5 pages.
Russian Office Action in Russian Application No. 2010134158, dated Jun. 23, 2013, 12 pages (with English translation).
Sajki et al., "The role of anti-obesic in the treatment of metabolic syndrome," Journal of Clinical Experimental Medicine, 2005, 213(6):643-649 (with English abstract).
Santarus, Inc., Cycloset Prescribing Information, 2010, 13 pages.
Santarus, Inc., Santarus Announces Commercial Launch of of Novel Type 2 Diabetes Drug Cycloset, 2010, 3 pages.
Schaper et al., "Peripheral vascular disease and Type 2 diabetes mellitus," Diabetes Metab Res Rev, 2000, 16(Suppl 1) S11-S15.
Schobel et al, "Effects of Bromocriptine on Cardiovascular Regulation in Healthy Humans," Hypertension, 1995, 25:1075-1082.
Schojaei et al., "Buccal Mucosa as a route for systemic drug delivery: A Review," J Pharm Pharmaceutical Science, 1998, 1(1):15-30.
Scirica et al., "Saxagliptin and cardiovascular outcomes in patients with type 2 diabetes mellitus," The New England Journal of Medicine, Oct. 3, 2013, 369(14):1317-1326.
Scranton et al., "A randomized, double-blind, placebo-controlled trial to assess safety and tolerability during treatment of type 2 diabetes with usual diabetes therapy and either Cycloset or placebo," BMC Endocrine Disorders, 2007, 7 pages.
Second Office Action in CN Application No. 200880025452.8, dated Mar. 28, 2013, 15 pages (with English translation).
Stout, "Insulin as a mitogenic factor: role in the pathogenesis of cardiovascular disease," The American Journal of Medicine, Feb. 21, 1991, 90 (suppl 2A):62S-65S.
Supplementary Search Report in EP Application No. EP03772024.0, dated Oct. 10, 2007, 3 pages.
Supplementary Search Report in EP Application No. 03785088.0, dated Jan. 10, 2008, 9 pages.
Suresh et al., "Intranasally delivered microdoses of bromocriptine (BCR) effectively reduces serum prolactin levels in hyperprolactinaemic patients," Current Sci, 1995, vol. 68, pp. 528-531.
Takasawa, "Inhibition of dipeptidyl peptidase 4 regulates microvascular endothelial growth induced by inflammatory cytokines," Biochemical and Biophysical Research Communications, 2010, 401:7-12.
The Lipid, 2005, 16(3):265-270 (with English abstract).
Third Office Action in CN Application No. 200880025452.8, dated Feb. 10, 2014, 8 pages (with English translation).
Tsagarakis et al., "Effectiveness of a long-lasting injectable form of bromocriptine in patients with prolactin and growth hormone secreting macroadenomas," Clinical Endocrinol, 1995, vol. 42, pp. 593-599.
Turner, "Intensive blood-glucose control with sulphonylureas or insulin compared with conventional treatment and risk of complications in patients with type 2 diabetes (UKPDS 33)," UK Prospective Diabetes Study D (UKPDS) Group, The Lancet, Sep. 12, 1998, 352:837-853.
Valente et al., "Metabolite involvement in Bromocriptine-induced prolactin inhibition in rats," J Pharmacol Expt Therapeutics, 1997, vol. 282, pp. 1418-1424.
Vermesh et al., "Vaginal Bromocriptine: Pharmacology and Effect on Serum Prolactin in Normal Women," Obstet Gynecol, 1988, vol. 72, pp. 693-697.
Veroscience, LLC, Prior Approval Supplement for CMC Change Utilization of Micronized Bromocriptine Mesylate (Redacted), 2010, 22 pages.
White et al., "Alogliptin after acute coronary syndrome in patients with type 2 diabetes," The New England Journal of Medicine, Oct. 3, 2013, 369(14):1327-1335.

(56) References Cited

OTHER PUBLICATIONS

Wimalasena et al., "Chiral multisubstrate inhibitors of dopamine β-monooxygenase: evidence for dual modes of interaction," American Chemical Society/Biochemistry, vol. 36, 1997, pp. 7144-7153.
Zhang et al., "Bromocriptine/skf38393 treatment ameliorates dyslipidemia in ob/ob mice," Metabolism, 1999, 48(8):1033-1040.
Zhang et al., "Inhibitory effects of bromocriptine on vascular smooth muscle cell proliferation," Atherosclerosis, 1997, 133:37-44 (Abstract only—1 page).
Zhang et al., "Inhibitory effects of bromocriptine on vascular smooth muscle cell proliferation," Atherosclerosis, 1997, 133:37-44 (Full article).
Zou et al., "Protein-protein coupling/uncoupling enables dopamine d2 receptor regulation of AMPA receptor-mediated excitotoxicity," The Journal of Neuroscience, Apr. 27, 2005, 25(17):4385-4395.
Office Action in JP Application No. 2012-514225, dated Jun. 26, 2014, 7 pages (with English translation).
Decision of Rejection in JP Application No. 2012-514225, dated Apr. 28, 2015, 9 pages (with English tanslation).
Office Action in AU Application No. 2010256366, dated Jun. 25, 2013, 4 pages.
Office Action in CN Application No. 201080028010.6, dated Sep. 26, 2013, 16 pages (with English translation).
Rejection Decision in CN Application No. 201080028010.6, dated Jun. 13, 2014, 16 pages (with English translation).
Office Action in EP Application No. 10784223.9, dated Oct. 30, 2015, 6 pages.
Extended European Search Report in EP Application No. 10784223.9, dated Sep. 27, 2012, 16 pages.
International Preliminary Report on Patentability in International Application No. PCT/US2010/037605, dated Dec. 6, 2011, 5 pages.
International Search Report and Written Opinion in International Application No. PCT/US2010/037605, dated Jul. 28, 2010, 6 pages.
Office Action in CO Application No. 13-132846, dated Jun. 12, 2014, 3 pages188.
Extended European Search Report in EP Application No. 118431881, dated Apr. 1, 2014, 7 pages.
CA Office Action in CA Application No. 2749611, dated Nov. 27, 2015, 3 pages.
Final Office Action in U.S. Appl. No. 12/402,694, dated Dec. 18, 2015, 28 pages.
Dotto et al. (Clinical pharmacokinetics of cabergoline.Clin Pharmacokinet. 2003;42(7):633-45).

THERAPEUTIC PROCESS FOR THE TREATMENT OF THE METABOLIC SYNDROME AND ASSOCIATED METABOLIC DISORDERS

CROSS-REFERENCE TO RELATED APPLICATIONS

This application is a Divisional of U.S. patent application Ser. No. 13/200,127 filed Sep. 19, 2011 which is a Continuation-in-Part of U.S. patent Ser. No. 10/944,617 filed Sep. 17, 2004, which in turn is a Continuation-in-Part of U.S. patent application Ser. No. 10/635,841 filed Aug. 6, 2003, which claims the benefit of U.S. Provisional Application No. 60/402,231 filed Aug. 9, 2002, the disclosure of each of which is incorporated herein by reference in its entirety, for all purposes.

BACKGROUND OF THE INVENTION

1. Field of the Invention

The present invention is directed to therapeutic processes for the treatment of obesity and associated metabolic disorders such as the metabolic syndrome, and more particularly to a planned dietary regimen that can treat obesity, metabolic syndrome, prediabetes, and Type 2 diabetes.

2. Brief Description of the Art

The incidence of overweight and obese occurrences in the U.S. and worldwide human population is reaching epidemic proportions. Obesity (commonly defined as a Body Mass Index of >30 $kg/m^2$) is often associated with a variety of pathologic conditions such as hyperinsulinemia, insulin resistance, diabetes, hypertension, and dyslipidemia, and each of these conditions contributes to the risk of cardiovascular disease. Collectively, these pathologies that tend to associate (obesity, insulin resistance, dyslipidemia, and hypertension) have been termed "the metabolic syndrome" and are a major risk factor for cardiovascular disease. More recently, the U.S. National Cholesterol Education Program has classified Metabolic Syndrome as meeting three out of the following five criteria: fasting glucose level of at least 110 mg/dl, plasma triglyceride level of at least 150 mg/dl (hypertriglycerdemia), HDL cholesterol below 40 mg/dl in men or below 50 mg/dl in women, blood pressure at least 130/85 mm Hg (hypertension), and central obesity, with central obesity being defined as abdominal waist circumference greater than 40 inches for men and greater than 35 inches for women. The American Diabetes Association estimates that 1 in every 5 overweight people suffer from Metabolic Syndrome.

According to the guidelines of the American Diabetes Association, to be diagnosed with Type 2 diabetes, an individual must have a fasting plasma glucose level greater than or equal to 126 mg/dl or a 2-hour oral glucose tolerance test (OGTT) plasma glucose value of greater than or equal to 200 mg/dl (Diabetes Care, 26:S5-S20, 2003). A related condition called pre-diabetes is defined as having a fasting glucose level of greater than 100 mg/dl but less than 126 mg/dl or a 2-hour OGTT plasma glucose level of greater than 140 mg/dl but less than 200 mg/dl. Mounting evidence suggests that the pre-diabetes condition may be a risk factor for developing cardiovascular disease (Diabetes Care 26:2910-2914, 2003). Pre-diabetes, also referred to as impaired glucose tolerance or impaired fasting glucose is a major risk factor for the development of type 2 diabetes mellitus, cardiovascular disease and mortality. Much focus has been given to developing therapeutic interventions that prevent the development of type 2 diabetes by effectively treating prediabetes (Pharmacotherapy, 24:362-71, 2004).

Although pharmaceutical medications exist for the treatment of diabetes, dyslipidemia, obesity, and hypertension, the combined use of such medications for the treatment of the metabolic syndrome suffer many disadvantages. Frequently, a regimen of medications to treat these pathologies is impractical, unsafe, and only modestly effective in the long term. No singular long-term effective pharmaceutical treatment for the metabolic syndrome currently exists.

A second approach to the treatment of this disorder is nutritional intervention leading to the reduction of excess adiposity (adipose tissue) via a calorie restricting diet. Inasmuch as a reduction of obesity has consistently been demonstrated to improve various pathologies of the metabolic syndrome, prodigious efforts have been made to formulate a nutritional plan that may be effective in the long-term treatment of the syndrome in the general population. The development of an optimal dietary plan to treat the metabolic syndrome has proven an elusive task. There are several reasons for this shortcoming. First, the metabolic rate of calorie-restricted obese individuals quickly decreases to match the reduced energy intake and equilibrium is reached before a reduced ideal body weight is attained. Upon an increase in food consumption following this occurrence, body fat stores cycle often back above pretreatment levels. Secondly, the source of energy in many diets is high carbohydrate/low fat in content, that can exacerbate specific aspects of the syndrome. Thirdly, empirical evidence indicates that calorie restricting dietary plans are difficult to adhere to long-term and most individuals regain weight lost on such diets within 5 years. Most importantly, an enormous body of scientific evidence indicates that the control of metabolism including the development and the reversal of the metabolic syndrome resides within the central nervous system, and is largely independent of the caloric content of the diet.

Studies of vertebrate species in the wild that undergo annual cycles of metabolism oscillating between the metabolic syndrome and normal metabolism indicate that adjustable alterations of neuroendocrine activities regulated by the hypothalamus play major roles in the regulation of metabolism. For example, many vertebrate species will undergo annual cycles of body fat store level without any change in food consumption whatsoever during the year. Moreover, many species are fattest during seasons of greatest energy expenditure, such as during the migratory periods of the year. Therefore, it is not possible to ascribe increased body fat store level in these animals strictly to increased energy input or decreased energy expenditure levels. The change in body composition appears to be a function of changes in metabolic biochemical pathways operative at different seasons. Animals increase or decrease their fat to lean mass ratio by fractionally increasing lipid synthesis or protein turnover, respectively, without necessarily having to alter energy balance.

During the fattening periods of the year, it has been observed that many species develop symptoms of the metabolic syndrome (i.e., hyperinsulinemia, insulin resistance, hyperlipidemia, and glucose intolerance) analogous to the human situation. Research in this area has identified key components of this endogenous mechanism for the regulation of metabolism (Luo, S. et al., NeuroReport vol. 8:3495-3499, 1997; Luo, S. et al., Neuroendocrinology vol. 68:1-10, 1998; Luo, S. et al, NeuroReport vol. 10, 2073-2077, 1999; Cincotta, A. H. et al., Am. J. Physiol. 278:R435-R444, 2000; Boundy, V. A. et al., Am. J. Physiol. 279:R505-R514, 2000;

Luo, S. et al., Neuroendocrinology vol 69:160-166, 1999; Bina, K. G. et al., Neuroendocrinology vol. 71:68-78, 2000; Kraszewski, K. Z. et al., Int. J. Molecular Med. vol: 5:349-355, 2000). These include interactions within specific nuclei of the hypothalamus that orchestrate autonomic-neuroendocrine events that in turn interact variably to produce different organismal level physiologies (i.e., normal metabolism or the metabolic syndrome) as a function of their interaction.

By identifying differences in these neural circuits between seasonal obese, insulin resistant animals and lean, insulin sensitive animals, one may be able to identify etiologic factors in the natural development of the syndrome. Collectively, such studies may suggest that decreases in the dopamine to norepinephrine activity ratio in the hypothalamus, and especially increased noradrenergic activity within the ventromedial hypothalamus, are key neuronal components driving the induction of the metabolic syndrome irrespective of energy intake in study animals. Additional components in the syndrome include increases in the activity of corticotropin releasing hormone to stimulate the pituitary-adrenal axis and the sympathetic nervous system via the dorsomedial hypothalamus, and hypothalamic increases in neuropeptide Y activity. Such neuronal alterations concurrently stimulate increases in parasympathetic and sympathetic neuronal activities leading to increased insulin hyper-secretion, hepatic glucose production, lipid synthesis, and lipolysis (Bina, K. G. et al., Neuroendocrinology vol. 71: 68-78, 2000). As a result, the organism fattens, and becomes insulin resistant, hyperlipidemic, and hypertensive (i.e., develops the metabolic syndrome).

Although pharmacologic agents acting as neuromodulators may be applied locally to appropriate neurons in the brain to induce or reverse the metabolic syndrome by mimicking the natural neuronal activities driving each condition, it is not a practical approach to the treatment of the disorder.

U.S. Pat. No. 6,004,972 to Cincotta et al., discloses a process for the long term modification and regulation of lipid and carbohydrate metabolism—generally to reduce obesity, insulin resistance, and hyperinsulinemia or hyperglycemia, or both, by administration of a dopamine agonist, such as bromocriptine.

U.S. Pat. No. 5,877,183 to Cincotta discloses methods for the regulation and modification of lipid and glucose metabolism by administering a dopamine D1 agonist, optionally in combination with a dopamine D2 agonist, an alpha-1 adrenergic antagonist, an alpha-2 adrenergic agonist, or a serotonergic inhibitor, or optionally in combination with a dopamine D2 agonist coadministered with at least one of alpha-1 adrenergic antagonist, an alpha-2 adrenergic agonist, or a serotonergic inhibitor, and further administering a serotonin $5HT_{1b}$ agonist.

U.S. Pat. Nos. 5,744,477 and 5,760,047 both issued to Cincotta et al. disclose an improvement in a method of weight and/or body-fat reduction comprising a preferably moderate reduction in the caloric intake of a subject in need of such treatment in combination with administration of a prolactin inhibitor. Additionally, this patent discloses a method for altering and/or resetting prolactin profiles and thereby controlling one or more metabolic disorders such as obesity, excessive body fat, hyperlipidemia, hyperlipoproteinemia, hyperglycemia, hypercholesterolemia, hyperinsulinemia, insulin resistance, glucose intolerance, and Type II diabetes.

U.S. Pat. No. 5,585,347 issued to Cincotta et al, discloses methods for detecting abnormalities in prolactin daily rhythms. The disclosed methods involve comparing a prolactin profile of a vertebrate (including a human) subject being tested that has been compiled over a predetermined period to a predetermined standard prolactin profile for healthy subjects U.S. Pat. No. 5,344,832 issued to Cincotta et al. discloses a process for the long term modification and regulation of lipid and glucose metabolism to reduce obesity, insulin resistance, and hyperinsulinemia or hyperglycemia, or both, by administration of a dopamine agonist and a prolactin stimulator. The dopamine agonist and prolactin stimulator are administered in daily dosages, respectively, at a time of day dependent on the normal circadian rhythm of fat and lean members of a similar species.

What is needed in the art is an effective dietary method of treating obesity, the metabolic syndrome, and its associated disorders, including Type 2 diabetes, that is simple to implement and takes into account the neuronal effects that can influence regulatory centers for metabolism. The present invention is believed to be an answer to that need.

SUMMARY OF THE INVENTION

In one aspect, the present invention is directed a method of treating a patient suffering from the metabolic syndrome, obesity, Type 2 diabetes, pre-diabetes, hypertension, dyslipidemia, insulin resistance, endothelial dysfunction, pro-inflammatory state, pro-coagulative state, or any combination thereof, comprising the steps of: (a) providing to the patient suffering from metabolic syndrome, obesity, Type 2 diabetes, pre-diabetes, hypertension, dyslipidemia, insulin resistance, endothelial dysfunction, pro-inflammatory state, and pro-coagulative state a dietary regimen that decreases overactive CNS noradrenergic tone; followed by (b) providing to the patient a dietary regimen that increases dopaminergic tone while maintaining the decreased overactive CNS noradrenergic tone.

In another aspect, the present invention is directed to an article of manufacture comprising packaging material and one or more food products contained within the packaging material, wherein the one or more food products are effective for decreasing overactive CNS noradrenergic tone and wherein the packaging material comprises a label which indicates that the one or more food products can be used for treating metabolic syndrome, obesity, Type 2 diabetes, pre-diabetes, hypertension, dyslipidemia, insulin resistance, endothelial dysfunction, pro-inflammatory state, pro-coagulative state, or a combination thereof, in a patient, and wherein the one or more food products are selected from the group consisting of:

1) protein of about 25%±5% of total daily caloric intake of the patient;

2) monounsaturated fat of about 25%±5% of total daily caloric intake of the patient, 3) saturated fat of about 5%±5% of total daily caloric intake of the patient;

4) polyunsaturated fat of about 3%±5% of total daily caloric intake of the patient; and 5) complex carbohydrate of about 42%±7% of total daily caloric intake of the patient;

and combinations thereof.

In another aspect, the present invention is directed to an article of manufacture comprising packaging material and one or more food products contained within the packaging material, wherein the one or more food products are effective for increasing dopaminergic tone while maintaining decreased overactive CNS noradrenergic tone, and wherein the packaging material comprises a label which indicates that the one or more food products can be used for treating metabolic syndrome, obesity, Type 2 diabetes, pre-diabetes, hypertension, dyslipidemia, insulin resistance, endothelial dysfunction, pro-inflammatory state, pro-coagulative state, or a combination thereof, in a patient, and wherein the one or more food products are selected from the group consisting of:

1) protein of about 24%±5% of total daily caloric intake of the patient;
2) monounsaturated fat of about 23%±5% of total daily caloric intake of the patient;
3) saturated fat of about 5%±5% of total daily caloric intake of the patient;
4) polyunsaturated fat of about 3%±5% of total daily caloric intake of the patient;
5) complex carbohydrate of about 45%±5% of total daily caloric intake of the patient;
6) L-DOPA-containing food in an amount sufficient to ingest about 25-400 mg. of L-DOPA per day;
and combinations thereof.

In another aspect, the present invention is directed to a method of treating a patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state, comprising the steps of: (a) providing to the patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state a food product that decreases overactive CNS noradrenergic tone; wherein the food product that decreases overactive CNS noradrenergic tone comprises:

1) protein intake of about 25%±5% of total daily caloric intake;
2) monounsaturated fat intake of about 25%±5% of total daily caloric intake;
3) saturated flit intake of about 5%±5% of total daily caloric intake;
4) polyunsaturated fat intake of about 3%±5% of total daily caloric intake;
5) complex carbohydrate intake of about 42%±7% of total daily caloric intake; and
6) total caloric intake set at 15-25% less than the patient's daily energy expenditure; followed by (b) providing to the patient a food product that increases dopaminergic tone while maintaining the decreased overactive CNS noradrenergic tone; wherein the food product that increases dopaminergic tone while maintaining the decreased overactive CNS noradrenergic tone comprises:

1) protein intake of about 24%±5% of total daily caloric intake;
2) monounsaturated fat intake of about 23%±5% of total daily caloric intake;
3) saturated fat intake of about 5%±5% of total daily caloric intake;
4) polyunsaturated fat intake of about 3%±5% of total daily caloric intake;
5) complex carbohydrate intake of about 45%±7% of total daily caloric intake;
6) total caloric intake set at 0-25% less than the patient's daily energy expenditure; and
7) L-DOPA-containing foods in an amount sufficient to ingest about 20-400 mg of L-DOPA per day; and wherein the polyunsaturated fat intake in each of steps (a) and (b) individually comprise a ratio of omega-3 to omega-6 polyunsaturated fatty acids from between about 0.25:1 to about 2:1; and wherein the providing step (a) continues for approximately 4 to 12 weeks; and wherein the providing step (b) continues for approximately 4 to 6 months.

In another aspect, the present invention is directed to a food product effective for treating a patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state, the food product comprising: (a) nutrients that decreases overactive CNS noradrenergic tone; and (b) nutrients that increases dopaminergic tone while maintaining the decreased overactive CNS noradrenergic tone, These and other aspect will be described in more detail in the following detailed description of the invention.

DETAILED DESCRIPTION OF THE INVENTION

It has been unexpectedly discovered by the present inventor that macro- and micro-nutrients may act as neuronal modulators and influence regulatory centers for metabolism. In other words, the foods consumed on a daily basis may influence metabolism not as a function of their caloric content but rather indirectly through modulating the control centers for metabolism in the brain. It is believed that adherence to the dietary plan will improve neuroendocrine regulation of metabolism and lead to a reduction of symptoms of the metabolic syndrome as well as related disorders such as obesity, Type 2 diabetes, pre-diabetes, hypertension, dyslipidemia, insulin resistance, endothelial dysfunction, pro-inflammatory state, and pro-coagulative state.

In seasonal animals (e.g., those animals whose physiology changes predictably and in an ordered fashion as a function of the time of the year; see Meier, A. H. and Cincotta, A. H., Diabetes Reviews, Vol. 4: 464-487, 1996 for a review), the quality of foods available for consumption changes seasonally. Even though the annual cycle of physiology is endogenous, it can be potentiated by seasonal changes in food quality. The present inventor has unexpectedly discovered that macronutrient and micronutrient influences on central control centers for metabolism are characteristic of many vertebrate species including animals such as humans. Therefore, it is believed that it is possible to influence the primary regulator of metabolism (the brain) via appropriate alterations in food quality intake and thereby influence overall metabolism. Such alterations in metabolism can be effective in treating obesity, and associated diseases such as hyperinsulinemia, cardiovascular disease, insulin resistance, diabetes, hypertension, dyslipidemia, and the like.

The hypothalamic activities described above that potentiate the metabolic syndrome induce the following neuroendocrine changes in the periphery relative to normal individuals: (1) increases in sympathetic tone, e.g., increased plasma norepinephrine to dopamine neurotransmitter or neurotransmitter metabolite ratio; (2) decreased morning urinary melatonin metabolite levels; (3) increases in plasma insulin and glucagon levels before and insulin levels during a glucose tolerance test; (4) increases in plasma norepinephrine and norepinephrine metabolite levels during the glucose tolerance test; (5) increases in plasma cortisol levels; and (6) increases in the plasma or urinary norepinephrine basal level and/or in response to corticotrophin releasing factor. A daily nutritional dietary intake regimen in accordance with the present invention is believed to be effective in reducing these hypothalamic activities and thereby treating obesity, diabetes, the metabolic syndrome, and it's associated diseases.

As defined herein, the term "dietary regimen" refers broadly to packaged or unpackaged food product provided to a patient for consumption in accordance with the method of the present invention, or information in any form communicated to a patient that instructs the patient about packaged or unpackaged foods that should be consumed (e.g., dietary counseling). The term "metabolite" refers to a cellular breakdown product of a selected compound, such as a neurotransmitter. The term "regular food" and "ordinary food", used herein interchangeably, refers to food that is not part of the packaged food items of the invention. Furthermore, in the method of the present invention, the phrase "overactive CNS noradrenergic tone" refers to overactive central nervous system noradrenergic tone, and is exemplified in part by overactive sympathetic tone.

As indicated above, the present invention is directed to methods of treating a patient suffering from obesity, metabolic syndrome and/or related disorders, including Type 2 diabetes, comprising a dietary regimen that decreases overactive CNS noradrenergic tone; followed by a dietary regimen that increases dopaminergic tone while maintaining the decreased overactive CNS noradrenergic tone. Each of these dietary regimens and their associated effects are discussed in more detail below.

Since each patient's individual condition and metabolic characteristics are unique, it is desirable, although not always necessary, to first evaluate the patient's central neuronal activities so that a baseline of the patient's metabolism can be established. This evaluation is done by several means, including, but not limited to, obtaining a medical history of the patient, conducting a physical examination of the patient, calculating the patient's daily energy expenditure (e.g, Harris-Benedict equation and/or indirect calorimetry), and determining the patient's ideal body weight (e.g., insurance table of ideal body weight based on height and weight measurements and percent body fat composition, age, and sex). In addition, it is desirable to conduct a blood test to evaluate the patient's perhipheral neuroendocrine factors. Such a blood test would preferably include an analysis (e.g., a determination of the amounts) of (a) plasma norepinephrine and norepinephrine metabolite, insulin, dopamine and dopamine metabolite levels before and/or during a glucose tolerance test (GTT), (b) plasma cortisol levels, (c) morning urinary melatonin metabolite, norepinephrine or norepinephrine metabolite levels, and/or (d) plasma norepinephrine or norepinephrine metabolite levels, generally in response to corticotropin releasing factor. Another marker that may be of potential value in evaluating neuronal activities is plasma serotonin or plasma serotonin metabolite levels (e.g, 5-HIAA, 5-hydroxy-indole acetic acid). Comparing the amounts of these surrogate markers between normal and metabolic syndrome subjects will delineate the neuroendocrine "blueprint" to be reestablished by dietary intervention in metabolic syndrome subjects. In addition, periodic inspections of these markers during the course of dietary intervention will allow for re-adjustment of the dietary plan to achieve optimal success in improving metabolism.

In one embodiment, the dietary regimen that decreases overactive CNS noradrenergic tone (hereinafter referred to as Stage 1) preferably includes:
1) protein intake of about 25%±5% of total daily caloric intake;
2) monounsaturated fat intake of about 25%±5% of total daily caloric intake;
3) saturated fat intake of about 5%±5% of total daily caloric intake;
4) polyunsaturated fat intake of about 3%±5% of total daily caloric intake;
5) complex carbohydrate intake of about 42%±7% of total daily caloric intake; and
6) total caloric intake set at 15-25% less than the patient's daily energy expenditure.

More preferably, the dietary regimen that decreases overactive CNS noradrenergic tone includes:
1) protein intake of about 25%±3% of total daily caloric intake;
2) monounsaturated fat intake of about 25%±3% of total daily caloric intake;
3) saturated fat intake of about 5%±3% of total daily caloric intake;
4) polyunsaturated fat intake of about 3%±3% of total daily caloric intake;
5) complex carbohydrate intake of about 42%±5% of total daily caloric intake; and
6) total caloric intake set at 15-20% less than the patient's daily energy expenditure.

Nutrients that decreases overactive CNS noradrenergic tone include pantethine, neuronal noradrenaline synthesis inhibitors, neuronal postsynaptic noradrenergic receptor blockers, neuronal presynaptic noradrenaline reuptake enhancers, neuronal presynaptic noradrenaline receptor stimulators, neuronal presynaptic noradrenaline release inhibitors, noradrenaline degradation enzyme stimulators, neuronal postsynaptic noradrenaline signal transduction inhibitors, and combinations thereof.

The length of time spent in Stage 1 is determined from the blood test results established prior to beginning the dietary regimen. In general, when either (a) the plasma norepinephrine, norepinephrine metabolite, and/or insulin levels, (b) morning urinary norepinephrine metabolite levels, (c) glucose tolerance norepinephrine levels, or (d) plasma norepinephrine to dopamine neurotransmitter or neurotransmitter metabolite ratio are reduced at least 20% of initial values, the individual is ready to begin Stage 2 of the program. This process generally takes approximately 4 to 12 weeks depending on the individual.

At the end of Stage 1, sympathetic nervous system activities overactive in the metabolic syndrome will become reduced towards normal levels, thus improving metabolism. This can be evidenced in part via measures of plasma norepinephrine metabolite and norepinephrine levels before and during a glucose tolerance test as mentioned above. At this time, the dietary regimen that increases dopaminergic tone while maintaining decreased overactive CNS noradrenergic tone (hereinafter referred to as Stage 2) commences, and preferably includes one or more of the following:
1) protein intake of about 24%±5% of total daily caloric intake;
2) monounsaturated fat intake of about 23%±5% of total daily caloric intake;
3) saturated fat intake of about 5%±5% of total daily caloric intake;
4) polyunsaturated fat intake of about 3%±5% of total daily caloric intake;
5) complex carbohydrate intake of about 45%±7% of total daily caloric intake;
6) total caloric intake set at 15-25% less than the patient's daily energy expenditure; and
7) L-DOPA-containing foods (such as Broad beans) in an amount sufficient to ingest about 20-400 mg of L-DOPA per day.

More preferably, the Stage 2 dietary regimen includes one or more of the following:

1) protein intake of about 24%±3% of total daily caloric intake;
2) monounsaturated fat intake of about 23%±3% of total daily caloric intake;
3) saturated fat intake of about 5%±3% of total daily caloric intake;
4) polyunsaturated fat intake of about 3%±3% of total daily caloric intake;
5) complex carbohydrate intake of about 45%±5% of total daily caloric intake;
6) total caloric intake set at 15-20% less than said patient's daily energy expenditure; and
7) L-DOPA-containing foods (such as Broad beans) in an amount sufficient to ingest about 20-300 mg, of L-DOPA per day.

Nutrients that increase dopaminergic tone include L-DOPA, neuronal dopamine synthesis stimulators, neuronal postsynaptic dopaminergic receptor stimulators, neuronal presynaptic dopamine reuptake inhibitors, neuronal presynaptic dopamine receptor blockers, neuronal presynaptic dopamine release enhancers, dopamine degradation enzyme inhibitors, neuronal postsynaptic dopamine signal transduction stimulators, and combinations thereof.

Most preferably, the L-DOPA-containing foods in item (7) above are provided in an amount sufficient to ingest about 20-150 mg of L-DOPA per day. In one preferred embodiment, the L-DPOA-containing foods may be consumed throughout the day to effectuate a day-long rise in the circulating L-DOPA level.

As indicated above, Stage 2 includes the introduction of foods rich in L-DOPA (dihydroxyphenylalanine) such as broad beans, fava beans and the like. It is believed that such foods ingested following stage 1 of this nutritional regimen allow for a further increase in the central dopamine to norepinephrine activity ratio, and further improves metabolism by reducing parasympathetic and sympathetic activities towards normal. Ingestion of L-DOPA containing foods without the prior exposure to the Stage 1 diet of this plan will not provide benefit of improving the metabolic syndrome inasmuch as the L-DOPA will be converted to norepinephrine centrally, which could function to maintain the syndrome. A second advantage of this methodology for treating the metabolic syndrome is that metabolic rate decreases typically observed with other calorie restricting diets are not observed with this nutritional weight loss plan, thus allowing a gradual, steady and prolonged weight loss. Energy intake dispensation is channeled away from lipid synthesis (and storage) and towards protein turnover. Consequently, the body lean to fat mass ratio increases which helps deter the metabolic syndrome.

Stage 2 of the program may be modified to improve metabolism based again on surrogate marker test results. In general, periodic increases in monounsaturated fat and/or protein content of the diet may be necessary for the progression towards re-establishment of the normal neuroendocrine profile that maintains normal metabolism.

Like Stage 1, the length of time spent in Stage 2 is determined from the blood test results established prior to beginning the dietary regimen. In general, Stage 2 continues for approximately 4 to 6 months.

Preferably, at each stage during the program, simple sugars and/or high glycemic index carbohydrates are not to be consumed concurrently with saturated fats at a weight ratio greater than 1 carbohydrate to 4 saturated fat. In addition, in both Stage 1 or Stage 2, polyunsaturated fat intake may further comprise a ratio of omega-3 to omega-6 polyunsaturated fatty acids from between about 0.25:1 to about 2:1. In addition, it is preferred, but not required, that the food product be administered within 4 hours of waking in the morning.

In an alternative embodiment, a serotonin precursor may also be administered as part of the dietary regimen. Useful serotonin precursors include L-tryptophan, L-5-hydroxytryptophan, and the like. Useful doseages generally range from about 50 to about 2000 mg. Preferably, the serotonin precursor is administered in the evening before bedtime.

In order to assist the patient in consuming the proper foods at each stage of the dietary regimen, and to provide confidence that the patient is following the prescribed dietary regimen, the present invention also includes prepackaged meals and/or recipes that provide the proper balance of protein, carbohydrate, fat, total calories, and, if appropriate, the proper amount of L-DOPA. In one embodiment, the invention contemplates an article of manufacture comprising packaging material and one or more food products contained within the packaging material, wherein the one or more food products are effective for decreasing overactive CNS noradrenergic tone (Stage 1 of the above dietary regimen). The packaging material comprises a label which indicates that the food products can be used for treating the metabolic syndrome and/or related disorders in a patient, and wherein the food products comprise one or more of the following:

1) protein of about 25%±5% of total daily caloric intake of the patient;
2) monounsaturated fat of about 25%±5% of total daily caloric intake of the patient;
3) saturated fat of about 5%±5% of total daily caloric intake of the patient;
4) polyunsaturated fat of about 3%±5% of total daily caloric intake of the patient; and
5) complex carbohydrate of about 42%±7% of total daily caloric intake of the patient.

In another embodiment, the invention contemplates an article of manufacture comprising packaging material and one or more food products contained within the packaging material, wherein the food products are effective for increasing central dopamine to norepinephrine activity ratio (Stage 2 of the above dietary regimen). The packaging material comprises a label which indicates that the food products can be used for treating the metabolic syndrome and/or related disorders in a patient, and wherein the food products comprise one or more of the following:

1) protein of about 24%±5% of total daily caloric intake of the patient;
2) monounsaturated fat of about 23%±5% of total daily caloric intake of the patient;
3) saturated fat of about 5%±5% of total daily caloric intake of the patient;
4) polyunsaturated fat of about 3%±5% of total daily caloric intake of the patient;
5) complex carbohydrate of about 45%±5% of total daily caloric intake of the patient;
6) L-DOPA-containing food in an amount sufficient to ingest about 20-400, and more preferably about 20-300 mg. of L-DOPA per day.

In either embodiment of the articles of manufacture recited above, the polyunsaturated fat may further comprise a ratio of omega-3 to omega-6 polyunsaturated fatty acids from between about 0.25:1 to about 2:1.

As an alternative embodiment, the packaged food products may contain only part (e.g., one, two, or three) of the above-recited components with instructions for the patient to consume or obtain the remaining components from other sources (e.g., regular food). However, the total caloric value of the food products, in combination with regular food (if any), is approximately 0-25% less, and more preferably, 0-20% less, than the patient's daily energy expenditure.

In the above packaged food product embodiments, the present invention also contemplates including instructions on the label informing the purchaser how to consume the packaged food products in order to derive benefit from the dietary regimen. As defined herein, a food product include packaged foods, prepared meals, food bars, drinks, condiments, and the like.

The present invention is further described in detail by means of the following Example. All parts and percentages are by weight, and all temperatures are degrees Celsius unless explicitly stated otherwise.

EXAMPLE

Patients suffering from obesity or a related disorder such as hyperinsulinemia, insulin resistance, diabetes, hypertension, dyslipidemia, or metabolic syndrome are subjected to the following treatment program:
1. Obtain medical history of patient;
2. Conduct physical exam;
3. Calculate daily energy expenditure;
4. Determine ideal body weight;
5. Conduct blood work to determine the neuroendocrine status of the patient;
6. Devise Stage 1 nutritional plan and describe to patient;
7. Provide pre-packaged meals and/or recipes to patient to achieve Stage 1 nutritional goals;
8. Conduct weekly follow-up of patient compliance and general health;
9. Conduct blood work to determine response to Stage 1 nutritional plan, readiness for initiation of Stage 2 plan, and improvements in metabolic syndrome (e.g., changes in plasma glucose, insulin, total cholesterol, LDL cholesterol, and free fatty acid levels, body weight and blood pressure);
10. Provide pre-packaged meals and/or recipes to patient to achieve Stage 2 nutritional goals;
11. Conduct bi-weekly follow-up of subject compliance and general health;
12. Conduct blood work to evaluate the improvement to the neuroendocrine axis and metabolism; and
13. Conduct physical exam to evaluate improvement to general health and test for improvement in metabolic syndrome parameters.

Patients following the above regimen should observe gradual improvement in metabolism and a reduction in the symptoms of the metabolic syndrome, obesity, and Type 2 diabetes.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A food product effective for treating a patient suffering from a condition selected from the group consisting of metabolic syndrome, obesity, type 2 diabetes, pre-diabetes, hypertension, dyslipidemia, insulin resistance, endothelial dysfunction, pro-inflammatory state, and procoagulative state, said food product comprising:

(a) nutrients that decrease overactive CNS noradrenergic tone selected from the group consisting of pantethine, neuronal noradrenaline synthesis inhibitors, neuronal postsynaptic noradrenergic receptor blockers, neuronal presynaptic noradrenaline reuptake enhancers, neuronal presynaptic noradrenaline receptor stimulators, neuronal presynaptic noradrenaline release inhibitors, noradrenaline degradation enzyme stimulators, neuronal postsynaptic noradrenaline signal transduction inhibitors, and combinations thereof; and (b) nutrients that increase dopaminergic tone selected from the group consisting of L-DOPA, neuronal dopamine synthesis stimulators, neuronal postsynaptic dopaminergic receptor stimulators, neuronal presynaptic dopamine reuptake inhibitors, neuronal presynaptic dopamine receptor blockers, neuronal presynaptic dopamine release enhancers, dopamine degradation enzyme inhibitors, neuronal postsynaptic dopamine signal transduction stimulators, and combinations thereof.

2. The food product of claim 1, further comprising:
1) protein of about 25%±5% of total daily caloric intake;
2) monounsaturated fat of about 25%±5% of total daily caloric intake;
3) saturated fat of about 5%±5% of total daily caloric intake;
4) polyunsaturated fat of about 3%±5% of total daily caloric intake; and
5) complex carbohydrate of about 42%±7% of total daily caloric intake.

3. The food product of claim 1, further comprising:
1) protein of about 24%±5% of total daily caloric intake;
2) monounsaturated fat of about 23%±5% of total daily caloric intake;
3) saturated fat of about 5%±5% of total daily caloric intake;
4) polyunsaturated fat of about 3%±5% of total daily caloric intake; and
5) complex carbohydrate of about 45%±7% of total daily caloric intake.

4. The food product of claim 2, wherein said polyunsaturated fat further comprises omega-3 and omega-6 polyunsaturated fatty acids, present in a ratio of omega-3 to omega-6 polyunsaturated fatty acids of from between about 0.25:1 to about 2:1.

5. The food product of claim 1, wherein said food product is selected from the group consisting of packaged foods, prepared meals, food bars, drinks, condiments, and combinations thereof.

6. The food product of claim 3, wherein the nutrient that increases dopaminergic tone is L-DOPA, and said L-DOPA is present in an amount of between 20-400 mg.

7. The food product of claim 3, wherein said polyunsaturated fat further comprises omega-3 and omega-6 polyunsaturated fatty acids, present in a ratio of omega-3 to omega-6 polyunsaturated fatty acids of from between about 0.25:1 to about 2:1.

8. The food product of claim 2, wherein said food product provides between 75 and 85% of said patient's daily energy expenditure.

9. The food product of claim 3, wherein said food product provides between 75 and 100% of said patient's daily energy expenditure.

10. The food product of claim 1 wherein the nutrient that increases dopaminergic tone is L-DOPA.

11. The food product of claim 10 wherein the nutrient that decreases overactive CNS noradrenergic tone is pantethine.

12. The food product of claim 1 wherein the nutrient that decreases overactive CNS noradrenergic tone is pantethine.

* * * * *